United States Patent [19]

Pichierri

[11] Patent Number: 5,618,529

[45] Date of Patent: *Apr. 8, 1997

[54] DIAPER RASH TREATMENT

[76] Inventor: Virgil F. Pichierri, 50 Brigham Hill Rd., Grafton, Mass. 01519

[*] Notice: The term of this patent shall not extend beyond the expiration date of Pat. No. 5,194,261.

[21] Appl. No.: 321,203

[22] Filed: Oct. 11, 1994

Related U.S. Application Data

[63] Continuation of Ser. No. 30,769, Mar. 15, 1993, abandoned, which is a continuation of Ser. No. 879,533, May 4, 1992, Pat. No. 5,194,261, which is a continuation of Ser. No. 618,395, Nov. 27, 1990, abandoned.

[51] Int. Cl.$^6$ ........................................... A61K 7/40
[52] U.S. Cl. ................ 424/78.06; 424/78.2; 424/401; 514/865; 523/105
[58] Field of Search ...................... 514/865; 424/401, 424/78.2, 78.06; 523/105

[56] References Cited

U.S. PATENT DOCUMENTS

| | | | |
|---|---|---|---|
| 3,876,771 | 4/1975 | Denner | 424/78.06 |
| 4,007,263 | 2/1977 | Pichierri | 424/401 |
| 4,350,785 | 9/1982 | Habib | 524/55 |
| 4,382,919 | 5/1983 | Alonso et al. | 424/47 |
| 4,556,560 | 12/1985 | Buckingham | 514/865 |
| 4,569,955 | 2/1986 | Dhabhar | 523/120 |
| 4,728,642 | 3/1988 | Pawelchak et al. | 424/445 |
| 4,758,630 | 7/1988 | Shah et al. | 525/207 |
| 4,816,254 | 3/1989 | Moss | 514/865 |
| 4,857,321 | 8/1989 | Thomas | 514/865 |
| 4,910,247 | 3/1990 | Haldar et al. | 524/400 |
| 4,948,580 | 8/1990 | Browning | 424/78.2 |
| 4,996,238 | 2/1991 | Matavers | 514/865 |
| 5,073,604 | 12/1991 | Holeva et al. | 525/327.8 |
| 5,194,261 | 3/1993 | Pichierri | 424/401 |

FOREIGN PATENT DOCUMENTS

| | | |
|---|---|---|
| 0048556 | 3/1982 | European Pat. Off. . |
| 0260859 | 3/1988 | European Pat. Off. . |

OTHER PUBLICATIONS

Editio Cantor, Aulendorf/Wurtt: Bundesverband der Pharm. Industrie E.V. "Rote Liste", No. 84089, 1987, p. 84.

*Primary Examiner*—Amy Hulina
*Attorney, Agent, or Firm*—David H. Judson

[57] ABSTRACT

An improved method of treating diaper rash in both infants and adults is described. The method entails coating the affected area with a composition containing a copolymer of a lower alkyl vinyl ether and maleic acid, or a derivative of the copolymer.

2 Claims, No Drawings

DIAPER RASH TREATMENT

CROSS REFERENCE TO RELATED APPLICATION

This is a continuation of application U.S. Ser. No. 08/030,769 filed on Mar. 15, 1993, now abandoned, which application is a continuation of U.S. Ser. No. 07/879,533, filed on May 4, 1992, now U.S. Pat. No. 5,194,261, which application is a continuation of U.S. Ser. No. 07/618,395, filed on Nov. 27, 1990, now abandoned.

BACKGROUND OF THE INVENTION

Diaper rash is an inflammation of the skin in the diaper area of neonates, infants, children, and incontinent adults. It is generally believed caused by the metabolic by-products of both urine and feces. Currently available treatments for diaper rash are generally based upon the use of zinc oxide, vitamins (A, D, and D3), or some combination thereof. These active ingredients are incorporated into a cream or salve by blending them into various purified semisolid ointment bases, e.g. mineral oil, petrolatum, soft paraffin, lanolin, and the like. While these treatments are often times effective for treating routine, simple diaper rashes, severe cases of diaper rash, especially those often observed with incontinent adults, have proved resistant to the treatments.

Accordingly, there is a need for an improved diaper rash treatment, particularly for use in severe cases.

The primary component of the compositions used herein for the improved treatment of diaper rash is a copolymer of a lower alkyl vinyl ether and maleic acid. U.S. Pat. Nos. 3,003,988 and 4,393,080 disclose the use of the copolymer and derivatives thereof as an adhesive for fixing dentures or ostomy devices to mucous membranes. U.S. Pat. No. 4,910,247 discloses a blend of a mixed salt of the copolymer in combination with a stearic acid metal salt as an improved adhesive for denture and ostomy use. U.S. Pat. No. 3,876,771 discloses a skin protection gel for use in protecting a stoma from fecal matter and still active gastric juices, which gel contains 25 to 95% isopropanol along with the monoisopropyl ester of the copolymer. U.S. Pat. No. 4,007,263 discloses a method of relieving irritation of skin (due to fecal drainage) surrounding an iliac stoma by applying thereto a composition containing at least 40% of a calcium, sodium partial mixed salt of the copolymer in a petroleum jelly base. U.S. Pat. No. 4,728,642 discloses a method of treating wounds by packing a wound emitting a large amount of fluid with granular material and then covering the wound site with an adhesive layer containing in part the copolymer or a derivative thereof. European Appln. 0,260,859 discloses a medicated skin composition containing the copolymer, isopropyl alcohol, citric acid ester plasticizer, and a specific antimicrobial agent.

Accordingly, the copolymer and its derivatives, while having been found to have utility as an adhesive, for protecting and relieving irritation from fecal matter (normally neutral or slightly alkaline) around a stoma, as part of an adhesive layer over a wound, and as a carrier/adhesive for an antimicrobial agent, has not been used as a treatment for diaper rash or to relieve skin irritation caused by contact with urine (normally slightly acidic), its metabolic by-products, infant feces (usually acidic), and its metabolic by-products.

It is thus an object of the present invention to produce a treatment for and inhibition of diaper rash in neonates, infants, children, and incontinent adults, which treatment is effective even in severe cases of diaper rash.

SUMMARY OF THE INVENTION

The present invention comprises treating a diaper rash in which urine and/or its metabolic by-products are the cause of or a contributing factor to the rash. More particularly, in one embodiment of the invention for the treatment of severe diaper rash the invention entails applying to a situs of the severe diaper rash a composition comprising about 15 to 40% of a copolymer, or derivative thereof, of a lower alkyl vinyl ether and maleic acid dispersed in a semisolid ointment base, overcoating the copolymer composition with a layer of a semisolid water-insoluble ointment base, and allowing the copolymer composition to remain essentially intact for an extended period of time, generally through several diaper changes. Healing of the skin is generally observed within about 1 to 4 days. The overcoating layer is removed and then reapplied with each successive diaper change. Periodically, e.g. daily, the copolymer composition is removed (if it comes off easily) to inspect the skin and reapplied. In an alternative embodiment of the invention for the treatment of minor diaper rash as well as to inhibit the development of diaper rash, the invention entails applying at each diaper change a coating to the skin in the diaper area of a composition comprising about 5 to 20% of a copolymer, or a derivative thereof, of a lower alkyl vinyl ether and maleic acid dispersed in a semisolid ointment base.

DETAILED DESCRIPTION OF THE INVENTION

The present diaper rash treatment utilizes a composition comprising a copolymer of a lower alkyl ($C_1$–$C_3$) vinyl ether and maleic acid or a derivative thereof, dispersed in a semi-solid ointment base.

Suitable copolymers for use herein are commercially available from GAF Corporation, Wayne, N.J., and are currently sold under the trademark GANTREZ®. The copolymers are preferably used in the form of a derivative thereof in which one or both of the acid groups have been converted to a metal salt or an alkyl ester. Suitable metal salts include calcium, sodium, and mixtures thereof. Suitable alkyl groups for the esters include propyl, isopropyl, butyl, isobutyl, and mixtures thereof. Generally about 20 to 90%, preferably about 70 to 90% for the metal salt and about 30 to 45% for the ester, of the initial carboxyl groups are reacted. The copolymers generally have a molecular weight of about 18,000 to 80,000 daltons (as measured by membrane osmometry in a 2-butanone 1@10 grams/1000 ml solution). The currently most preferred copolymer derivative is the mixed calcium and sodium salt blend supplied as GANTREZ® MS-955 wherein the proportion of Ca:Na is about 5–6:1 and the molecular weight is about 65,000–70,000. Other examples of specific copolymers useful herein include S-97 (intact acid groups), AN-169 (anhydride), ES-335 (monoisopropyl ester), ES-435 (monobutyl ester), and ES-425 (monobutyl ester).

The semisolid ointment base in which the copolymer is dispersed and which serves to prevent the copolymer from becoming too hard in use may be any such material conventionally used as a vehicle for medicinal substances for topical application. Suitable water-insoluble ointment bases for use herein include petrolatum, white petrolatum, lanolin, and the like. Suitable water-soluble ointment bases for use herein include polyethylene glycol polymers and the like. Preferably a water-insoluble ointment base is used because the water-soluble bases may in some instances be irritating to inflamed tissue as is present with a diaper rash.

Additional ingredients which may be present in the copolymer composition include oils such as mineral oil, fish liver oil, and cod liver oil; emollients such as glycerin, olive oil, and lanolin; fillers such as cellulose gum, calcium carbonate, karaya gum, gum tragacanth, gum acacia, carboxymethyl cellulose, and polyvinyl acetate; vitamins such as vitamins A, D, and D3; astringents such as zinc oxide and aluminum acetate; protectants such as Peruvian balsam; coloring agents; odorants; and other materials which are conventionally used in relieving skin irritation.

Preferably the compositions used herein are alcohol-free since alcohol, which can be absorbed systemically, can be fatal to neonares and is likely to cause burning and be an irritant to previously irritated skin.

The viscosity of the compositions used herein has not been found to be critical, and thus the specific viscosity of the composition will be selected merely as a matter of convenience. Generally any conventional cream or ointment viscosity may be used with variations merely affecting the ease of application. Generally, however, compositions used for treatment of severe diaper rash will have a higher viscosity than those used for inhibiting and/or treating mild diaper rash.

Compositions particularly useful for treating severe cases of diaper rash, i.e. in which the skin is denuded, excoriated, ulcerated and/or severely inflamed, generally contain about 15 to about 40 weight percent of the copolymer, preferably about 20 to about 35 weight percent. The additional ingredients may be present in total amounts of up to about 50 weight percent, preferably up to about 30 weight percent. The balance of the composition is one or more semisolid ointment bases.

To utilize the compositions for severe diaper rash, they should be liberally applied over the specific irritation sites and then allowed to remain in place for an extended period of time, generally for several diaper changes. Healing generally has been noted to occur in about 1 to 4 days. To allow the treatment composition to remain in place for the extended period as well as to minimize any potential trauma and discomfit to the patient from repetitive removals of the composition and to prevent undue adherence to a diaper placed thereover, it has been found convenient to apply a coating of a semi-solid water-insoluble ointment base, e.g. petrolatum or lanolin, atop the treatment composition. The ointment base top coating can then be removed for cleaning purposes and then reapplied for successive rediaperings while allowing the treatment composition to remain essentially undisturbed. Periodically, e.g. daily, the treatment composition should be removed to inspect the skin and additional composition applied if healing is not complete. During the periodic replacement of the treatment composition, if it does not readily detach from the skin it should be allowed to remain in place for an additional period to prevent trauma to the patient. When healing is complete, or earlier, the treatment composition may be completely removed by the conventional use of soap and water.

Compositions particularly useful for inhibiting the development of diaper rash and for treating mild cases thereof, i.e. in which the skin is slightly red, sore, warm to the touch, and/or the commencement of inflammation is evident, generally contain about 5 to 20 weight percent of the copolymer, preferably about 8 to 15 weight percent. The additional ingredients may then be present in amounts of up to about 60 weight percent, preferably up to about 40 weight percent. The balance of the composition is one or more semisolid ointment bases.

To utilize the inhibiting and mild treatment compositions, they will generally be applied at a diaper change and then removed and reapplied at subsequent diaper changes in the same manner as other diaper rash products are currently utilized. If desired, an overcoating of a semi-solid water-insoluble ointment base may be applied atop the treatment composition.

During use of the copolymer compositions it is currently believed that the copolymer component becomes at least partially hydrated which causes it both to adhere to the skin and to form a firmly adhered barrier against diaper rash causative and irritant agents. While diaper rash is believed caused primarily by the metabolic by-products of wastes in general, there are acidic components of urine and infant stools which are not present in adult feces and are particularly irritating. Urine consists of approximately 93–97% water and 3–7% solids which include urea, uric acid (20 to 40 gm/day), creatine (methylgly-cocyamine; 0 to 40 mg/day in men and 0 to 80 mg/day in women), creatinine (lmethylglycocyamidine; the end product of creatine metabolism; 15 to 25 mg/kg of body weight/day), ammonia (0.5 to 1.3 gm/day), and inorganic substances such as chlorides, calcium, magnesium, and phosphorous. Urine is normally slightly acidic. Feces, on the other hand, of adults is normally neutral or slightly alkaline while that of infants is slightly acidic. It is the acidic agents which are believed to be highly irritating in the diaper area.

In the following non-limiting examples of diaper rash treating compositions and the use thereof, all parts and percents are by weight unless otherwise specified.

EXAMPLE I

An 8 month old congenital cardiac patient had a continuing diaper rash for over 2 months. Various therapies, including antifungals were tried over this period without success.

Inspection of the skin indicated an underlying fungal infection as well as several areas of epidermal denudation. A single application of an antifungal powder, i.e. MYCOSTATIN, followed by a conventional skin sealant, i.e. Bard wipe, to hold the powder in place was applied to the perineum. A treatment composition was prepared by blending and uniformly mixing 30.75% GANTREZ® MS-955, 15.4% cellulose gum, 5% mineral oil, 0.0224% peppermint oil, 0.017% D+C Red #27 Lake, 0.01% D+C Red #30 Lake, and white petrolatum q.s.

The treatment composition was applied over the skin sealant and surrounding areas in an amount sufficient to form a coating about 1–2 mm thick. No pain or discomfort was experienced by the patient during the application of the treatment composition. The coating was then overcoated with a layer of petrolatum jelly and a diaper placed thereover. At each diaper change, only the white petrolatum overcoating was removed, the patient cleaned, and a fresh over-coating applied, i.e. the treatment composition remained intact.

Within two days, this chronic diaper rash had started to resolve. After 7 days no diaper rash inflammation was still visible and the treatment composition was removed by the liberal use of soap and water.

EXAMPLE II

The procedure of Example I was repeated with an 8 month old ventilator dependent boy with medically managed Hirschprungs disease who was bothered by occasional diarrhea. Several therapies had been tried without success when the treatment composition of Example I was directly applied to the diaper area of the patient, overcoated with a layer of petroleum jelly, and a diaper placed thereover. At each diaper change, only the white petrolatum overcoating was removed, the patient cleaned, and a fresh over-coating applied, i.e. the treatment composition remained intact.

Within only 24 hours considerable improvement of the diaper rash was readily apparent. After 2 days no diaper rash inflammation was still visible and the treatment composition was removed by the liberal use of soap and water.

EXAMPLE III

A 6 year old oncology patient developed intractable diarrhea during a course of chemotherapy. Both his energy level and mobility were diminished. His appetite was poor but he received optimal calories via parental nutrition. Because of his diminished level of activity he wore diapers. Despite preventative perianal care being administered using a protective moisture barrier cream of Carrington Company as well as numerous alternative conventional treatments and cleansing with each diaper change, severe perianal denudation occurred.

The perianal area was cleaned with a mild antibacterial soap and inspected for signs of underlying fungal infection. The skin appeared free from fungal infection. The treatment composition of Example I was applied to the denuded skin and covered with a layer of petroleum jelly as in Example I. After, each diaper change was performed by cleansing (while leaving the treatment composition intact) and reapplying the petroleum jelly.

Remarkable improvement in skin integrity was apparent after 24 hours and essentially complete healing was evident after 7 days.

EXAMPLE IV

To inhibit the recurrence of the diaper rash on the patient of Example I, the following composition is applied and then removed on subsequent diaper changes: 10% GANTREZ® MS-955, 12% cellulose gum, 21% mineral oil, 10% lanolin, 3% zinc oxide, 0.0224% peppermint oil, and white petrolatum q.s. No recurrence is noted during a 20 day observation period.

EXAMPLE V

The following compositions are prepared for treating severe diaper rash:

| Ingredient | Amount | | | | | |
|---|---|---|---|---|---|---|
| | A | B | C | D | E | F |
| Gantrez® MS-955 | 25 | — | — | 10 | 15 | 20 |
| Gantrez® S-97 | — | 35 | — | — | 15 | — |
| Gantrez® ES-335 | — | — | 30 | — | — | 7 |
| Gantrez® ES-435 | — | — | — | 20 | — | 8 |
| Mineral oil | — | — | 5 | 2 | — | 1 |
| Cod liver oil | 4 | — | — | 10 | — | 1 |
| Cellulose gum | — | 12 | 10 | 8 | 18 | 4 |
| Calcium carbonate | 16 | — | 10 | — | 12 | — |
| Karaya gum | — | — | 4 | 12 | — | — |
| Vitamin A | 2 | — | 12 | — | — | 5 |
| Vitamin D | 2 | — | 6 | — | — | 2 |
| Aluminum Acetate | — | 7 | — | 5 | — | -2 |
| Colorant | — | — | — | — | 0.01 | 0.02 |
| Odorant | — | — | — | 0.1 | — | — |
| White petrolatum | qs | — | qs | — | — | qs |
| Lanolin | 5 | — | — | 11 | 20 | 2 |
| Petrolatum | — | qs | — | qs | qs | — |

The compositions are used as in Examples I–III for a variety of patients including neonares, infants, and adult incontinents. Similar results to those of the Examples are observed in each case.

EXAMPLE VI

The following compositions are prepared for regular use to inhibit diaper rash formation and to treat minor cases thereof:

| Ingredient | Amount | | | | | |
|---|---|---|---|---|---|---|
| | A | B | C | D | E | F |
| Gantrez® MS-955 | 5 | — | 10 | — | 15 | — |
| Gantrez® S-97 | 2 | 4 | — | 7 | 3 | 10 |
| Gantrez® ES-335 | — | 1 | 6 | — | — | — |
| Gantrez® ES-435 | 5 | — | — | 15 | — | — |
| Mineral Oil | 15 | — | 20 | — | 5 | 10 |
| Cod liver oil | 7 | 10 | — | — | 15 | — |
| Cellulose gum | — | 10 | 15 | — | — | 20 |
| Karaya gum | 2 | — | — | 12 | — | — |
| Vitamin A | — | — | 10 | — | 15 | — |
| Vitamin D | — | 5 | — | 8 | — | 12 |
| Aluminum Acetate | 7 | — | 12 | — | 20 | — |
| Colorant | — | 0.01 | — | — | 0.05 | — |
| Odorant | 0.1 | — | 0.05 | — | — | — |
| White petrolatum | q.s. | — | q.s. | — | q.s | — |
| Lanolin | 10 | — | 10 | — | 20 | 25 |
| Petrolatum | — | q.s. | — | q.s. | — | q.s. |

The compositions are used by application of a fresh coating with each diaper change to a group of 10 neonates. A second group of 10 neonates, used as a control, are washed thoroughly at each diaper change. After 10 days, the untreated neonates exhibit substantially increased incidence of diaper rash.

What is claimed is:

1. A method of treating a diaper rash which comprises the steps of:

applying to an area of diaper rash a composition about 5 to about 40% by weight of a mixture of copolymers of an alkyl vinyl ether, the copolymers having 1 to 3 carbon atoms in the alkyl group, and maleic acid and derivatives thereof selected from the group consisting of metal salts of calcium sodium and mixtures thereof and alkyl esters wherein the alkyl group is selected from the group consisting of propyl, isopropyl, butyl, isobutyl, and mixtures thereof, the mixture of copolymers being dispersed in a topically-acceptable carrier, the mixture of copolymers capable of reacting with waste by-products during use to become partially hydrated to thereby adhere to the skin and to form a barrier against diaper rash causative and irritant agents;

over-coating the composition with a layer consisting essentially of semi-solid ointment;

wherein when the mixture of copolymers becomes partially hydrated the over-coat layer prevents the composition from substantially adhering to a diaper surface; and removing and reapplying the over-coat layer during successive diaper changes while allowing the composition underlying said layer to remain essentially undisturbed throughout said successive diaper changes to thereby enable the skin to heal.

2. The method of claim 1, wherein the topically-acceptable carrier for the copolymer is selected from the group comprising water-insoluble and water-soluble ointment bases.

\* \* \* \* \*